United States Patent [19]

Herzig et al.

[11] Patent Number: 5,693,734
[45] Date of Patent: Dec. 2, 1997

[54] ORGANOSILICON COMPOUNDS CONTAINING FURANYL GROUPS

[75] Inventors: Christian Herzig, Taching am See; Bernward Deubzer, Burghausen; Martina Bloechl, Tann; Inge Seeger-Feichtinger, Stubenberg, all of Germany

[73] Assignee: Wacker-Chemie GmbH, Munich, Germany

[21] Appl. No.: 495,009

[22] Filed: Jun. 27, 1995

[30] Foreign Application Priority Data

Jun. 29, 1994 [DE] Germany .................. 44 22 833.3

[51] Int. Cl.[6] .................. C08G 77/04; C07F 7/18
[52] U.S. Cl. .................. 528/27; 549/214; 549/215
[58] Field of Search .................. 549/215, 214; 528/27

[56] References Cited

U.S. PATENT DOCUMENTS 4,656,235  4/1987  Tesoro et al. .................. 526/262
5,214,077  5/1993  Herzig et al. .................. 522/99

FOREIGN PATENT DOCUMENTS 0508491  10/1992  European Pat. Off. .
2093855   9/1982  United Kingdom .

OTHER PUBLICATIONS

Chemical Abstracts No. 84703, vol. 123, No. 8, 1995 pp. 949–952 Sincharge et al, "Silicon containing esters . . . ".
Database WPI, Week 6800, AN 68-26542Q pp. 12–20 Lukevits et al, "Preparing Photosensitive".
European Polymer Journal, vol. 24, Nr. 7, 1988, pp. 639–645 Mercier et al.
Journal of Organic Chemistry, vol. 32, No. 9, 1967, pp. 2841–2845, Hammann et al.
Chemical Abstracts No. 36511f, vol. 69, No. 10, 1968, p. 27 L.M. Pauthkov et al.
Chemical Abstracts No. 217152, vol. 97, No. 26, 1982 pp. 52–59 Svetkin et al., "Poly T3–furfanyl".

Chemical Abstracts No. 3584b, vol. 64, No. 3, 1966 pp. 490–498, Lukevics et al., "Hydroysilation".

*Primary Examiner*—Mark L. Berch
*Assistant Examiner*—Bruck Kifle
*Attorney, Agent, or Firm*—Martin Connaughton

[57] ABSTRACT

Organosilicon compounds containing furanyl groups which contain units of the formula

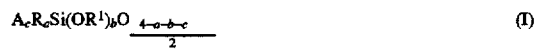 (I)

in which

R is identical or different and is a hydrogen atom or monovalent, SiC-bonded, aliphatically saturated, optionally substituted hydrocarbon radical, which can be interrupted by oxygen atoms, $R^1$ is identical or different and is an optionally substituted hydrocarbon radical having 1 to 8 carbon atoms, which can be interrupted by 1 to 3 oxygen atoms.

A is identical or different and is an SiC-bonded furanyl radical of the formula

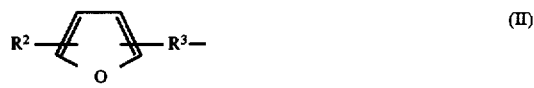 (II)

where $R^2$ has the meaning given above for the radical R and $R^3$ is a divalent hydrocarbon radical having 2 to 30 carbon atoms, which can contain one or more groups, chosen from the group consisting of

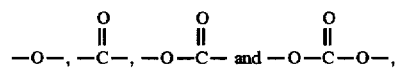

a is 0, 1, 2 or 3, b is 0, 1 or 2 and c is 0, 1 or 2, with the proviso that the sum a+b+c is less than or equal to 3 and the organosilicon compound contains at least one radical A per molecule.

4 Claims, No Drawings

ORGANOSILICON COMPOUNDS CONTAINING FURANYL GROUPS

FIELD OF INVENTION

The present invention relates to organosilicon compounds containing furanyl groups, processes for their preparation, crosslinkable compositions which comprise these organosilicon compounds containing furanyl groups, and crosslinked coatings produced therefrom.

BACKGROUND OF INVENTION

Furfuryloxysilanes which, because of their Si—O—C structure, are not stable to moisture and easily split off the furan ring from the Si atom are prepared from furfuryl alcohol and alkoxysilanes by the method of Thoru Takaya, Japan 5566 of Jul. 26, 1957. It is known that such furfuryloxysilanes give flexible coatings with acids over several hours at temperatures above 60° C. Reference may be made to Susumu Takatani, Japan 4094 of May 24, 1958. In general, stability toward environmental influences but in conjunction with complete curing within seconds does not exist.

According to Hammann et al., J. Org. Chem. 32, 2841-2 (1967), furan rings bonded directly to Si atoms are easily split off by traces of acid under the influence of heat.

Furanyl-substituted silanes can also be prepared by hydrosilylation. For example, Lukevics and Voronkov, Chemical Abstracts 64, 1966, 3584 added hydridosilanes onto 2-vinylfuran under platinum catalysis.

SUMMARY OF INVENTION

The present invention relates to organosilicon compounds containing furanyl groups having at least one Si—O—Si grouping.

The organosilicon compounds according to the invention containing furanyl groups are preferably those which contain units of the formula

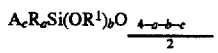  (I)

in which

R is identical or different and is a hydrogen atom or monovalent, SiC-bonded, aliphatically saturated, optionally substituted hydrocarbon radical, which can be interrupted by oxygen atoms, $R^1$ is identical or different and is an optionally substituted hydrocarbon radical having 1 to 8 carbon atoms, which can be interrupted by 1 to 3 oxygen atoms.

A is identical or different and is an SiC-bonded furanyl radical of the formula

  (II)

where $R^2$ has the meaning given above for the radical R and $R^3$ is a divalent hydrocarbon radical having 2 to 30 carbon atoms, which can contain one or more groups, chosen from the group consisting of

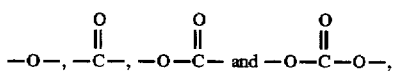

a is 0, 1, 2 or 3, b is 0, 1 or 2 and c is 0, 1 or 2, with the proviso that the sum a+b+c is less than or equal to 3 and the organosilicon compound according to the invention contains at least one radical A per molecule.

The radical R is preferably an aliphatically saturated, optionally halogenated hydrocarbon radical having 1 to 26 carbon atoms, which can be interrupted by 1 to 12 separate oxygen atoms, the methyl, ethyl and the phenyl radical being more preferred.

Examples of radicals R are alkyl radicals, such as the methyl, ethyl, n-propyl, iso-propyl, n-butyl, iso-butyl, tert-butyl, n-pentyl, iso-pentyl, neopentyl and tert-pentyl radical, hexyl radicals, such as the n-hexyl radical, heptyl radicals, such as the n-heptyl radical, octyl radicals such as the n-octyl radical and iso-octyl radicals, such as the 2,2,4-trimethylpentyl radical, nonyl radicals, such as the n-nonyl radical, decyl radicals, such as the n-decyl radical, dodecyl radicals, such as the n-dodecyl radical, and octadecyl radicals, such as the n-octadecyl radical, cycloalkyl radicals, such as cyclopentyl, cyclohexyl, cycloheptyl and methylcyclohexyl radicals, aryl radicals, such as the phenyl, napththyl, anthryl and phenanthryl radical, alkaryl radicals such as o-, m- and p-tolyl radicals, xylyl radicals and ethylphenyl radicals, and aralkyl radicals, such as the benzyl radical and the α- and β-phenylethyl radical.

Examples of halogenated radicals R are haloalkyl radicals, such as the 3,3,3-trifluoro-n-propyl radical, the 2,2,2,2',2'-hexafluoroisopropyl radical, and the heptafluoroisopropyl radical, and haloaryl radicals, such as the o-, m- or p-chlorophenyl radical.

Examples of radicals $R^1$ are the hydrocarbon radicals mentioned for the radical R, having 1 to 8 carbon atoms, and the 2-methoxyethyl radical.

The radical $R^1$ is preferably the methyl, ethyl or butyl radical, the methyl and ethyl radical being more preferred.

The preferred value for c is 0 or 1.

The radical $R^2$ is preferably a hydrogen atom.

Examples of the radical $R^3$ are *—$CH_2CH_2$—, *—$OCH_2CH_2$—, *—$CH_2OCH_2CH_2$—, *—$CH_2O(CH_2)_3$—, *—$CH_2O(CH_2)_6$—, *—$CH_2O(C_2H_4O)_n(CH_2)_3$— and *—$CH_2O(C_3H_6O)_n(CH_2)_3$— where n is 1 to 10,

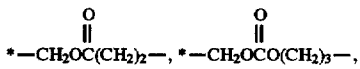

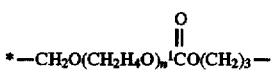

where $n^1$ is 1 to 5 *—$CH_2OCH_2CH=CH$—, *—$CH_2OCH_2C(=CH_2)$—, *—$CH_2O(C_2H_4O)_n$$CH_2CH=CH$— and *—$CH_2O(C_2H_4O)_n$$CH_2C(=CH_2)$—$_4$ where $n^1$ is 1 to 5 *—$CH_2OCH(CH_3)$—$O(C_2H_4O)_n$ $(CH_2)_m$— and *—$CH_2OCH(C_2H_5)O(C_2H_4O)_n(CH_2)_m$— where n is 1 to 10 and m is 2 or 3, and the side of the radical marked with * is bonded to the furan ring.

The radical $R^2$ is more preferably *—$CH_2O(CH_2)_3$— or *—$CH_2O(C_2H_4O)_{n^1}(CH_2)_3$— where $n^1$ is 1 to 5, and the side of the radical marked with * is bonded to the furan ring.

The radical A is preferably Z—$CH_2CH_2$—, Z—$CH_2OCH_2CH_2$—, Z—$CH_2O(CH_2)_3$—, Z—$CH_2O(C_2H_4O)_{n^1}(CH_2)_3$— or Z—$CH_2O(C_3H_6O)_{n^1}(CH_2)_3$—, where $n^1$ is 1 to 5, and in which Z is

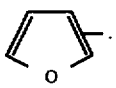

The organosilicon compounds according to the invention containing furanyl groups can be those which consist exclusively of units of formula (I), or copolymers of siloxane units of formula (I) and organic units or blocks of units which bond at least two Si atoms to one another chemically. The pure organic constituents of such organosiloxane copolymers are preferably linear or branched hydrocarbon radicals or oxygen-containing radicals, preferably polyether radicals. In these copolymers, the siloxane blocks are bonded to the organic units or blocks via the group Si—O—C or Si—C, but preferably via Si—C. Organic polyether bridges in these copolymers are more suitable for controlling the polarity of the furanylsilicon compounds according to the invention.

The organosilicon compounds according to the invention containing furanyl groups are more preferably those of the formula

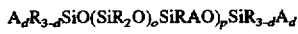

$$A_d R_{3-d} SiO(SiR_2O)_o SiRAO)_p SiR_{3-d} A_d \quad (III)$$

in which

A has the meaning given above,

R has the meaning given above in formula (I), with the exception of the hydrogen atom, d is identical or different and is 0 or 1, o is an integer from 1 to 1000 and p is 0 or an integer from 1 to 100, with the proviso that the organosilicon compound of formula (III) contains at least one radical A per molecule.

In formula (III), the o units —(SiR$_2$O)— and p units —(SiARO)— can be distributed in the organosiloxane molecule in any desired manner.

Examples of the organosilicon compounds according to the invention containing furanyl groups are copolymers of trimethylsiloxy, dimethylsiloxy and 3-furfuryloxypropyl-methylsiloxy units, copolymers of 3-furfuryloxypropyl-dimethylsiloxy, 3-furfuryloxypropyl-methylsiloxy and dimethylsiloxy units, copolymers of trimethylsiloxy, dimethylsiloxy and 3-(ω-furfuryl-oligo-ethyleneoxy-)propyl-methylsiloxy units, copolymers of trimethylsiloxy and 2-furylethyl units and cyclic siloxanes of 3-(ω-furfuryloligo-ethyleneoxy-)propyl-methylsiloxy units.

The organosilicon compounds according to the invention containing furanyl groups perferably have a viscosity at 25° C. of 20 to 5000 mm²/s, more preferably 100 to 1000 mm²/s.

The present invention relates to a process for the preparation of the organosilicon compounds according to the invention containing furanyl groups, which comprises reacting a furanyl compound (1) having at least one terminal aliphatic carbon-carbon multiple bond in which no furan ring carbon atom participates with an organosilicon compound (2) which contains at least one Si-bonded hydrogen atom.

The furanyl compound(1) is preferably of the formula

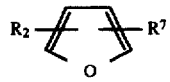

(VII)

in which R² has the above meaning and R⁷ is a monovalent hydrocardon radical having a terminal carbon-carbon multiple bond and having 2 to 30 carbon atoms, which can contain one or more groups, chosen from the group consisting of —O—, $$-\overset{O}{\underset{\|}{C}}-,\quad -O-\overset{O}{\underset{\|}{C}}-\quad -O-\overset{O}{\underset{\|}{C}}-O-.$$

Examples of the furanyl compounds (1) employed according to the invention are Z—CH=CH$_2$, Z—CH$_2$OCH=CH$_2$, Z—CH$_2$OCH$_2$CH=CH$_2$, Z—(CH$_2$)$_4$CH=CH$_2$, Z—CH$_2$O(C$_2$H$_4$O)$_n$CH$_2$CH=CH$_2$ and Z—CH$_2$O(C$_3$H$_6$O)$_n$CH$_2$CH=CH$_2$ where n is 1 to 5 and Z is

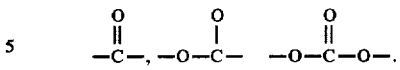

Processes for the preparation of the furanyl compounds (1) are known in organic chemistry.

The organosilicon compounds (2) employed according to the invention can be linear, branched or cyclic organosilicon compounds having at least one Si-bonded hydrogen atom which are known.

Organosilicon compounds (2) which are preferably employed are those which contain units of the formula

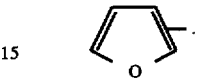

$$H_c R_a Si(OR^1)_b O_{\frac{4-a-b-c}{2}} \quad (IV)$$

in which

R has the meaning given in formula (I) with the exception of the hydrogen atom, and R¹, a, b and c have the meanings given above, with the proviso that the sum a+b+c is less than or equal to 3 and the organosilicon compound (2) employed according to the invention contains at least one Si-bonded hydrogen atom per molecule.

The organosilicon compounds (2) employed according to the invention are more preferably those of the formula

$$H_d R_{3-d} SiO(SiR_2O)_o(SiRHO)_p SiR_{3-d} H_d \quad (V),$$

in which

R has the meaning given in formula (I) with the exception of the hydrogen atom, and d, o and p have the meanings given above, with the proviso that the organosilicon compound of formula (III) contains at least one Si-bonded hydrogen atom per molecule.

In formula (V), the o units —(SiR$_2$O)— and p units —(SiHRO)— can be distributed in the organosiloxane molecule in any desired manner.

The content of Si-bonded hydrogen in the organosilicon compound (2) is preferably 0.02% to 1.60% by weight.

The organosilicon compound (2) employed according to the invention preferably have a viscosity at 25° C. of 0.5 to 20,000 mm²/s, more preferably 10 to 1000 mm²/s.

The organosilicon compounds (2) employed in the process according to the invention more preferably contain 2 to 20 Si-bonded hydrogen atoms per molecule.

Preferred examples of organopolysiloxanes of formula (V) are copolymers of dimethylhydridosiloxane and dimethylsiloxane units, copolymers of dimethylhydridosiloxane, dimethylsiloxane and methylhydridosiloxane units, copolymers of trimethylsiloxane and methylhydridosiloxane units and copolymers of trimethylsiloxane, dimethylsiloxane and methylhydridosiloxane units.

Processes for the preparation of organosilicon compounds having at least one Si-bonded hydrogen atom per molecule, are generally known.

In the process according to the invention, the organosilicon compound (2) is employed in an amount of preferably 0.5 to 1.5 Si—H groups, more preferably 0.7 to 1.1 Si—H groups, per terminal aliphatic carbon-carbon multiple bond of the furanyl compound (1).

The preparation of the organosilicon compounds according to the invention containing furanyl groups from a furanyl compound (1) and an organosilicon compound (2) containing Si-bonded hydrogen is preferably carried out using catalysts (3) which promote the addition of Si-bonded hydrogen on to a terminal, aliphatic carbon-carbon multiple bond.

Catalysts (3) which can be employed in the process according to the invention are the same catalysts which have been used to promote addition of Si-bonded hydrogen onto an aliphatic multiple bond.

The catalysts (3) are preferably a metal from the group of platinum metals or a compound or a complex from the group of platinum metals. Examples of such catalysts are metallic and finely divided platinum, which can be on supports, such as silicon dioxide, aluminum oxide or active charcoal, compounds and complexes of platinum, such as platinum halide, for example $PtCl_4$, $H_2PtCl_6.6H_2O$, $Na_2PtCl_4.4H_2O$, platinum-olefin complexes, platinum-alcohol complexes, platinum-alcoholate complexes, platinum-ether complexes, platinum-aldehyde complexes, platinum-ketone complexes, including reaction products of $H_2PtCl_6.6H_2O$ and cyclohexanone, platinum-vinylsiloxane complexes, such as platinum-1,3-divinyl-1,1,3,3-tetramethyldisiloxane complexes with or without a content of detectable inorganically bonded halogen, bis-(γ-picoline)-platinum dichloride, trimethylenedipyridineplatinum dichloride, dicyclopentadieneplatinum dichloride, dimethyl sulfoxideethyleneplatinum (II) dichloride and reaction products or platinum tetrachloride with an olefin and primary amine or secondary amine or primary and secondary amine according to U.S. Pat. No. 4,292,434, such as the reaction product of platinum tetrachloride dissolved in 1-octene with secbutylamine, and ammonium-platinum complexes according to EP-B 110 370, and compounds and complexes of rhodium, such as the rhodium complexes according to EP-A 476 426.

The catalyst (3) is preferably employed in amounts of 2 to 1000 ppm by weight (parts by weight per million parts by weight), preferably in amounts of 10 to 50 ppm by weight, calculated as elemental platinum and based on the total weight of furanyl compound (1) and organosilicon compound (2).

The process according to the invention is preferably carried out under the pressure of the surrounding atmosphere of about 900 to 1100 hPa; however it can be carried out under higher or lower pressures. The process is carried out at a temperature of 50° C. to 170° C., more 80° C. to 150° C.

Inert, organic solvents can be used in the process according to the invention, although the use of inert, organic solvents is not preferred. Examples of the inert organic solvents are toluene, xylene, octane isomers, butyl acetate, 1,2-dimethoxyethane, tetrahydrofuran and cyclohexane.

Excess furanyl compound (1) and any inert organic solvent used are preferably removed by distillation from the organo silicon compounds containing furanyl groups prepared by the process according to the invention.

In the process according to the invention, polycyclic derivatives can be formed as by-products from the furanyl compounds (1). For example, the formation of 7-oxatricyclic compounds and 7,9-dioxatricyclo[2.2.1.3]dec-2-ene is known from the reaction of the furanyl ring with another multiple bond in compound (1) in the context of a [2+4]-cyclo addition. Reference may be made to CA 113; 191204 d. The double bonds which remain may be reactive, in the ring system thus formed, towards Si-bonded hydrogen of the compound (2) under the conditions according to the invention, so that the organosilicon compounds containing furanyl groups may contain small amounts of units of the type mentioned.

The process according to the invention has the advantage that the preparation of silicon compounds which are rapidly cationically crosslinkable is carried out in a simple manner, and that regenerable starting substances, for example, furfuryl alcohol, which form the constituent which is actually reactive, can be used. In contrast to vinyl ethers, it is not possible to split off the reactive group from the Si-containing polymer or oligomer under hydrolytically acid conditions, which means that a loss of reactive groups in respect of hydrolysis is impossible.

The organosilicon compounds containing furanyl groups can be crosslinked cationically, for example by addition of acids, such as hydrochloric acids, sulfuric acids or p-toluenesulfonic acids. They are preferably crosslinked in a cationic polymerization initiated by light. Catalysts which are used for the crosslinking initiated by light are preferably onium salts, such as diaryliodonium salts or triarylsulfonium salts, which are known from EP-B 105 341 and DE 41 42 327 A (corrsp. U.S. Ser. No. 08/244,920, filed Jun. 8, 1994). Examples of such onium salts are the bis(dodecylphenyl) iodonium salts described in EP-B 105 341, such as bis-(dodecylphenyl)iodonium hexafluoroantimonate or bis-(dodecylphenyl)iodonium hexafluoroarsenate, or the iodonium salts described in DE 41 42 327 A, of the formula

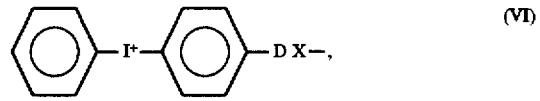

(VI)

in which D is a radical of the formula —O—$R^4$—$SiR^5_3$, in which $R^4$ is a divalent hydrocarbon radical having 1 to 18 carbon atoms, which is optionally interrupted by at least one oxygen atom and/or one sulfur atom and/or one carboxyl group, $R^5$ is a monovalent hydrocarbon radical having 1 to 18 carbon atoms, which is optionally interrupted by at least one oxygen atom, and $X^-$ is a tosylate anion or a weakly nucleophilic or non-nucleophilic anion $Y^-$ chosen from the group consisting of $CF_3CO_2^-$, $BF_4^-$, $PF_6^-$, $AsF_6^-$, $SbF_6^-$, $ClO_4^-$, $HSO_4^-$, $CF_3SO_3^-$ and $C_4F_9SO_3^-$.

The invention also relates to compositions which can be crosslinked by light, which comprise organosilicon compounds containing furanyl groups.

The organosilicon compounds according to the invention containing furanyl groups are preferably crosslinked by ultraviolet light having wavelengths in the range from 200 to 400 nm being preferred. The ultraviolet light can be generated, for example, in xenon, mercury low pressure, mercury medium pressure or mercury high pressure lamps. Light or "halogen light" having a wavelength of 400 to 600 nm is also suitable for the crosslinking by light. The organosilicon compounds according to the invention containing furanyl groups can also be crosslinked by light in the visible range if commercially available photosensitizers, such as 2-chlorothioxanthone, 2-isoropylthioxanthone, anthracene, perylene and phenothiazine, are also used.

The cationic polymerization of the organosilicon compounds containing furanyl groups can also be initiated by Brönsted or Lewis acids used for this purpose.

The crosslinking according to the invention is preferably carried out at a temperature of from 20° C. to 60° C. under a pressure of from 900 to 1100 hPa.

The organosilicon compounds containing furanyl groups and the compositions according to the invention have the advantage that, during storage and processing of the organosilicon compounds containing furanyl groups or of the compositions containing these compounds, no splitting off of reactive groups and conversion thereof into non-reactive components by moisture is observed.

The invention also relates to a process for the production of coatings, which comprises applying the compositions which can be crosslinked by light to a surface and allowing them to crosslink.

Examples of surfaces on to which the coatings can be applied are those of paper, wood, cork, films of plastic, for example, polyethylene films or polypropylene films, ceramic objects, glass, including glass fibers, metals, pasteboards, including those of asbestos, and woven and non-woven cloth of naturally occurring or synthetic organic fibers.

The application of the organosilicon compounds according to the invention containing furanyl groups to the surfaces to be coated can be carried out in any desired manner which is suitable for the production of coatings from liquid substances.

In the examples described below, all the data on parts and percentages relate to weight, unless stated otherwise. Unless stated otherwise, the following examples are carried out under a pressure of the surrounding atmosphere of about 1000 hPa, and at room temperature of about 20° C., or at a temperature which is established when the reactants are brought together at room temperature without additional heating or cooling.

All the viscosity data in the following examples relate to a temperature of 25° C.

(A) PREPARATION OF ALLYL FURFURYL ETHER 14 g of benzyltrimethylammonium chloride and 490 g of furfuryl alcohol are added in succession to 800 g of 50% strength sodium hydroxide solution at 45° C. 425 g of allylchloride are added dropwise over a period of about one hour, the reaction mixture heating up slowly and later boiling under reflux. The reaction is allowed to go to completion for an additional hour at a bottom temperature of about 80° C., and 100 ml of cyclohexane and 700 ml of water are added. The salt phase is separated off and the organic phase is washed 3 times with 200 ml of water and then freed from water by azeotropic distillation. The crude product is fractionated over a short column, 548 g of approximately 96% pure allyl furfuryl ether being obtained at 69° C. to 70° C./13 hPa, the structure of which is confirmed by the $^1$H-NMR spectrum (furfuryl signals at $\delta$=7.39; 6.33; 6.31; 4.45 ppm). The remaining 4% comprises dioxatricyclodecene as an internal cyclo addition product from the title compound.

(B) PREPARATION OF POLYETHYLENE GLYCOL ALLYL FURFURYL ETHER 600 g of NaOH are mixed with 600 ml of water and 14 g of benzyltrimethylammonium chloride and 1170 g of ethoxylated furfuryl alcohol (degree of ethoxylation 3.1) in succession, while stirring. A total of 450 g of allyl chloride are metered in at 70° C., the reaction mixture heating up constantly and gentle reflux starting. After two hours, the reaction ended, after which inorganic salts are dissolved in about one liter of water and separated off. The organic phase is washed twice with 200 ml of water each time, and distilled with addition of NaHCO$_3$, under 2 hPa without being fractionated. A total of 1100 g of slightly yellow distillate is obtained, the viscosity of which is 7.0 mm$^2$/s. The product corresponds to a homologous series of asymmetrically etherified oligo-ethylene glycols of the average formula (C$_4$H$_3$O)CH$_2$O(CH$_2$CH$_2$O)$_{2.75}$CH$_2$CH=CH$_2$. The triglycol allyl furfuryl ether can be identified as the most frequently occurring member of the homologous series in the GPC spectrum. 86% of the furanyl groups employed are obtained again by distillation; the degree of allylation is greater than 97%.

In the following, the abbreviation equ. means equivalent and mequ. means milliequivalent.

EXAMPLE 1

8 mg of platinum in the form of a 50% strength solution of platinum-1,3-divinyl-1,1,3,3-tetramethyldisiloxane complex in excess complexing ligand are added to 158 g of allylfurfurylether, the preparation of which is described above under (A). After addition of 0.5 g of NaHCO$_3$, a total of 270 g of an equilibrate of trimethylsiloxy, dimethylsiloxy and hydridomethylsiloxy units having a viscosity of 91 mm$^2$/s, the content of Si-bonded hydrogen of which is 0.37% by weight, are metered in under a nitrogen atmosphere at 85° C. in the course of about two hours. After an additional three hours at 83° C., more than 99% of the Si—H groups have been consumed. The reaction mixture is freed from volatile constituents at 120° C./3 hPa and filtered. A clear oil of viscosity 290 mm$^2$/s, which contains about 180 mequ. of furanyl groups per 100 g is obtained.

EXAMPLE 2

The procedure described in Example 1 is repeated, with the modification that instead of the equilibrate described in Example 1, 636 g of a siloxane polymer of hydridodimethylsiloxy, hydridomethylsiloxy and dimethylsiloxy units having a content of Si-bonded hydrogen of 0.157% by weigth and a viscosity of 135 mm$^2$/s is metered into the catalyzed allyl furfuryl ether. After the same reaction time and working up at 120° C./3 hPa, a clear, pale yellow oil having a viscosity of 700 mm$^2$/s is obtained. It can be seen from the $^1$H-NMR spectrum that the product has a furanyl equilvalent weight of about 1000 g. The proton resonances of the furan ring are at $\delta$=7.38; 6.31; 6.27 ppm and the SiCH$_2$ group formed is at $\delta$=0.50 ppm.

EXAMPLE 3

The procedure described in Example 1 is repeated with the modification that instead of the equilibrate described in Example 1, 2130 g of a siloxane polymer built up from trimethylsiloxy, dimethylsiloxy and hydridomethylsiloxy units and having 0.047% by weight of Si-bonded hydrogen and a viscosity of 90 mm$^2$/s is metered into the catalyzed allyl furfuryl ether. After volatile constituents have been removed at 120° C./3 hPa and after filtration, a clear, pale oil of viscosity 144 mm$^2$/s, which contains about 35 mequ. of furanyl groups in 100 g, is obtained.

EXAMPLE 4

20.4 g of polyglycol allyl methyl ether having an average degree of polymerization of 4.5 are initially introduced into the reaction vessel together with 36 g of allyl furfuryl ether. 0.5 ml of a 0.1N solution of KOH in ethanol and 30 g of xylene are added. After addition of 4.5 mg of platinum in the form of a 50% strength solution of platinum-1,3-divinyl-1, 1,3,3-tetramethyldisiloxane complex in excess complexing ligand, the mixture is heated to 110° C. under a nitrogen atmosphere and 159 g of a siloxane polymer of hydridodimethylsiloxy, hydridomethylsiloxy and dimethylsiloxy units having a content of Si-bonded hydrogen of 0.157% by weight and a viscosity of 135 mm$^2$/s are metered in. After a further two hours at the same temperature, the addition reaction has ended, and the solvent and excess ether are removed under a pressure of 5 hPa. A slightly colored oil of 420 mm²/s, which contains about 75 mequ. of furanyl groups and additionally 0.17 equ. of ethoxy units in 100 g is obtained.

EXAMPLE 5

59 g of the polyethyleneglycolallylfurfurylether of the average formula $(C_4H_3O)CH_2O(CH_2CH_2O)_{2.75}CH_2CH=CH_2$ prepared above under (B) are diluted with 45 ml of xylene. 5 mg of platinum are added in the form of a 50% strength solution of platinum-1,3-divinyl-1,1,3,3-tetramethyldisiloxane complex in excess complexing ligand, and the mixture is adjusted to a temperature of about 110° C. under a nitrogen atmosphere. A total of 95 g of a linear α,ω-dihydridodimethylpolysiloxane having a content of 0.21% of Si-bonded hydrogen are metered in over a period of one hour. When conversion is complete (after about 4 hours), the solvent and volatile contents are removed at 120° C./3 hPa. A highly liquid, yellowish oil of viscosity 36 mm²/s is obtained. According to the ¹H-NMR spectrum, the product contains 1.4 equ. of furanyl groups and about 3.7 equ. of ethoxy units per kg. The siloxane content of the polymer is 65% by weight.

EXAMPLE 6

63 g of the polyethylene glycol allyl furfuryl ether prepared above under (B) are mixed with 50 ml of xylene and 172 g of a siloxane polymer of viscosity 33 mm²/s at room temperature. The siloxane consists of trimethylsilyl, dimethylsilyl and hydridodimethylsilyl units and has a content of Si-bonded hydrogen of 0.116%. The mixture is heated to about 100° C. under an inert gas, and 3 mg of platinum in the form of a 50% strength solution of platinum-1,3-divinyl-1,1,3,3-tetramethyldisiloxane complex in excess complexing ligand are added to the vigorously stirred mixture. The solvent is removed at 120° C./3 hPa, whereupon a yellow oil of viscosity 91 mm²/s remains. ¹H-NMR analysis shows, per kg of polymer, 0.8 equ. of furan units and about 2.3 equ. of ethoxy units, with a siloxane contant of 77% by weight.

EXAMPLE 7

The organopolysiloxane containing furanyl groups which is obtained in Example 6 is mixed with 2%, based on the weight of the siloxane, of a 50% strength solution of bis(4-dodecylphenyl)iodonium hexafluoroantimonate in toluene and the mixture is applied in a layer thickness of about 4 μm to polyethylene film. UV- activated complete curing of this coating is carried out with a mercury medium pressure lamp (80 W/cm) at a distance of 10 cm for 0.3 second. The composition according to the invention is crosslinked to a solid, non-tacky coating.

What is claimed is:

1. An organosilicon compound containing furanyl groups consisting essentially of units of the formula

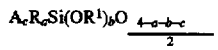     (I)

in which

R is identical or different and is a hydrogen atom or monovalent, SiC-bonded, aliphatically saturated, optionally halogen substituted hydrocarbon radical, which can be interrupted by oxygen atoms, R¹ is identical or different and is a hydrocarbon radical having 1 to 8 carbon atoms, of which 1 to 3 carbon - carbon bonds could be interrupted by an oxygen atom, A is identical or different and is an SiC-bonded furanyl radical of the formula

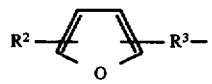     (II)

where R² has the meaning given above for the radical R and

R³ is a radical selected from the group consisting of
*—CH₂OCH₂CH₂—, *—CH₂O(CH₂)₃—, *—CH₂O(CH₂)₆—, *—CH₂O(C₂H₄O)ₙCH₂)₃— *—CH₂O(C₃H₆O)ₙ(CH₂)₃—

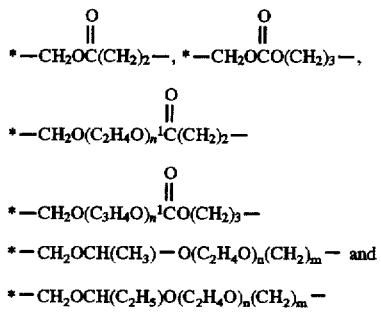

* —CH₂OCH(CH₃)—O(C₂H₄O)ₙ(CH₂)ₘ— and

* —CH₂OCH(C₂H₅)O(C₂H₄O)ₙ(CH₂)ₘ— a is 0, 1, 2 or 3,
b is 0, 1 or 2
c is 0, 1 or 2,
n is 1 to 10,
n¹ is 1 to 5, and
m is 2 or 3
with the proviso that the sum a+b+c is less than or equal to 3 and the organosilicon compound contains at least one radical A per molecule.

2. An organosilicon compound containing furanyl groups as claimed in claim 1, in which the radical R is an aliphatically saturated, optionally halogenated hydrocarbon radical having 1 to 26 carbon atoms, which can be interrupted by 1 to 12 separate oxygen atoms.

3. An organosilicon compound containing furanyl groups as claimed in claim 1, in which c is 0 or 1.

4. An organosilicon compound containing furanyl groups as claimed in claim 1, of the formula

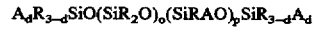     (III)

in which

A is identical or different and is an SiC-bonded furanyl radical of the formula

     (II)

where R² has the meaning given above for the radical R and

R³ is a radical selected from the group consisting of
*—CH₂OCH₂CH₂—, *—CH₂O(CH₂)₃—, *—CH₂O(CH₂)₆—, *—CH₂O(C₂H₄O)ₙ(CH₂)₃— *—CH₂O(C₃H₆O)ₙ(CH₂)₃—

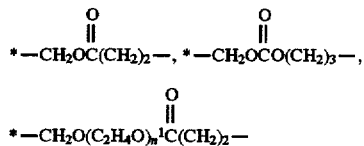

-continued

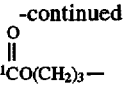

*—$CH_2OCH(CH_3)—O(C_2H_4O)_n(CH_2)_m$— and
*—$CH_2OCH(C_2H_5)O(C_2H_4O)_n(CH_2)_m$—

R is identical or different and is a monovalent, SiC-bonded aliphatically saturated, optionally halogen substituted hydrocarbon radical which can be interrupted by oxygen atoms, d is 0 or 1, o is an integer from 1 to 1000 and p is 0 or an integer from 1 to 100, with the proviso that the organosilicon compound of the formula (III) contains at least one radical A per molecule.

* * * * *